(12) United States Patent
Dachs, II et al.

(10) Patent No.: US 12,102,409 B2
(45) Date of Patent: Oct. 1, 2024

(54) ALIGNMENT AND ENGAGEMENT FOR TELEOPERATED ACTUATED SURGICAL INSTRUMENT

(71) Applicant: Intuitive Surgical Operations, Inc., Sunnyvale, CA (US)

(72) Inventors: Gregory W. Dachs, II, San Mateo, CA (US); Bruce Michael Schena, Menlo Park, CA (US)

(73) Assignee: Intuitive Surgical Operations, Inc., Sunnyvale, CA (US)

(*) Notice: Subject to any disclaimer, the term of this patent is extended or adjusted under 35 U.S.C. 154(b) by 778 days.

(21) Appl. No.: 16/840,730

(22) Filed: Apr. 6, 2020

(65) Prior Publication Data
US 2020/0229886 A1 Jul. 23, 2020

Related U.S. Application Data

(63) Continuation of application No. 15/121,369, filed as application No. PCT/US2015/020882 on Mar. 17, 2015, now Pat. No. 10,639,119.
(Continued)

(51) Int. Cl.
*A61B 46/10* (2016.01)
*A61B 1/00* (2006.01)
(Continued)

(52) U.S. Cl.
CPC .......... *A61B 46/10* (2016.02); *A61B 1/00142* (2013.01); *A61B 17/00234* (2013.01);
(Continued)

(58) Field of Classification Search
None
See application file for complete search history.

(56) References Cited

U.S. PATENT DOCUMENTS

| 4,542,272 A | 9/1985 | Hubbard et al. |
| 5,069,221 A | 12/1991 | Smith et al. |

(Continued)

FOREIGN PATENT DOCUMENTS

| CN | 1631622 A | 6/2005 |
| CN | 101203344 A | 6/2008 |

(Continued)

OTHER PUBLICATIONS

Extended European Search Report for Application No. EP19201778.8, mailed on Nov. 27, 2019, 5 pages.
(Continued)

*Primary Examiner* — Vicky A Johnson
(74) *Attorney, Agent, or Firm* — JONES ROBB, PLLC

(57) ABSTRACT

An instrument sterile adapter for coupling a surgical instrument and an instrument carriage includes an adapter control surface that extends control features of a control surface of the instrument carriage and receives an instrument control surface of the surgical instrument. A shaft receiving slot is positioned in the adapter control surface to receive an elongate tube of the surgical instrument when the adapter control surface receives the instrument control surface of the surgical instrument. The elongate tube may couple a proximal control mechanism of the surgical instrument to an end effector. The instrument sterile adapter may include a convex curved surface substantially perpendicular to and facing the adapter control surface to receive a corresponding concave curved surface on the instrument control surface. A bullet portion on the convex curved surface may engage a bullet receiving feature in the corresponding concave curved surface on the instrument control surface.

17 Claims, 9 Drawing Sheets

Related U.S. Application Data

(60) Provisional application No. 62/104,306, filed on Jan. 16, 2015, provisional application No. 62/103,991, filed on Jan. 15, 2015, provisional application No. 62/019,318, filed on Jun. 30, 2014, provisional application No. 61/954,571, filed on Mar. 17, 2014, provisional application No. 61/954,557, filed on Mar. 17, 2014, provisional application No. 61/954,595, filed on Mar. 17, 2014, provisional application No. 61/954,497, filed on Mar. 17, 2014, provisional application No. 61/954,502, filed on Mar. 17, 2014.

(51) Int. Cl.

| | | |
|---|---|---|
| *A61B 17/00* | (2006.01) | |
| *A61B 34/00* | (2016.01) | |
| *A61B 34/30* | (2016.01) | |
| *A61B 34/35* | (2016.01) | |
| *A61B 34/37* | (2016.01) | |
| *A61B 46/00* | (2016.01) | |
| *A61B 90/00* | (2016.01) | |
| *A61B 90/98* | (2016.01) | |
| *A61B 18/00* | (2006.01) | |
| *A61B 46/23* | (2016.01) | |
| *F16H 1/20* | (2006.01) | |

(52) U.S. Cl.
CPC .............. *A61B 34/30* (2016.02); *A61B 34/35* (2016.02); *A61B 34/37* (2016.02); *A61B 34/70* (2016.02); *A61B 46/40* (2016.02); *A61B 90/08* (2016.02); *A61B 90/361* (2016.02); *A61B 90/98* (2016.02); *A61B 2017/00477* (2013.01); *A61B 2018/00172* (2013.01); *A61B 46/23* (2016.02); *A61B 2090/0813* (2016.02); *F16H 1/20* (2013.01); *Y10T 29/49817* (2015.01); *Y10T 403/59* (2015.01)

(56) References Cited

U.S. PATENT DOCUMENTS

| | | | |
|---|---|---|---|
| 5,214,573 | A | 5/1993 | Roza |
| 5,469,863 | A | 11/1995 | Shah |
| 5,679,423 | A | 10/1997 | Shah |
| 5,803,086 | A | 9/1998 | Scholz et al. |
| 6,331,181 | B1 | 12/2001 | Tierney et al. |
| 6,471,172 | B1 | 10/2002 | Lemke et al. |
| 7,096,870 | B2 | 8/2006 | Lamprich et al. |
| 7,125,403 | B2 | 10/2006 | Julian et al. |
| 7,758,569 | B2 | 7/2010 | Brock |
| 7,947,050 | B2 | 5/2011 | Lee et al. |
| 7,963,913 | B2 | 6/2011 | Devengenzo et al. |
| 8,220,468 | B2 | 7/2012 | Cooper et al. |
| 8,506,555 | B2 | 8/2013 | Ruiz Morales |
| 8,529,582 | B2 | 9/2013 | Devengenzo et al. |
| 8,555,892 | B2 | 10/2013 | Traub |
| 8,998,930 | B2 | 4/2015 | Orban, III |
| 9,687,312 | B2 | 6/2017 | Dachs, II et al. |
| 9,839,487 | B2 | 12/2017 | Dachs, II et al. |
| 10,022,193 | B2 | 7/2018 | Cooper et al. |
| 10,045,828 | B2 | 8/2018 | Dachs, II et al. |
| 10,213,268 | B2 | 2/2019 | Dachs, II et al. |
| 10,278,784 | B2 | 5/2019 | Dachs, II |
| 10,363,109 | B2 | 7/2019 | Dachs, II et al. |
| 10,420,622 | B2 | 9/2019 | Dachs, II et al. |
| 10,485,621 | B2 | 11/2019 | Morrissette et al. |
| 10,537,400 | B2 | 1/2020 | Dachs, II et al. |
| 10,543,051 | B2 | 1/2020 | Schena et al. |
| 10,595,836 | B2 | 3/2020 | Smaby et al. |
| 10,610,320 | B2 | 4/2020 | Dachs, II et al. |
| 10,639,119 | B2 | 5/2020 | Dachs, II et al. |
| 10,898,288 | B2 | 1/2021 | Dachs, II et al. |
| 10,912,616 | B2 | 2/2021 | Dachs, II et al. |
| 11,045,274 | B2 | 6/2021 | Dachs, II et al. |
| 11,389,259 | B2 | 7/2022 | Dachs, II |
| 11,446,105 | B2 | 9/2022 | Dachs, II et al. |
| 2002/0032452 | A1 | 3/2002 | Tierney et al. |
| 2002/0111635 | A1 | 8/2002 | Jensen et al. |
| 2002/0143319 | A1 | 10/2002 | Brock |
| 2003/0216723 | A1 | 11/2003 | Shinmura et al. |
| 2004/0049205 | A1 | 3/2004 | Lee et al. |
| 2005/0119527 | A1 | 6/2005 | Banik et al. |
| 2005/0240178 | A1 | 10/2005 | Morley et al. |
| 2005/0244217 | A1 | 11/2005 | Burke et al. |
| 2005/0251110 | A1 | 11/2005 | Nixon |
| 2006/0235436 | A1 | 10/2006 | Anderson et al. |
| 2006/0260622 | A1 | 11/2006 | Wooley et al. |
| 2006/0273135 | A1 | 12/2006 | Beetel |
| 2007/0012135 | A1 | 1/2007 | Tierney et al. |
| 2007/0142825 | A1 | 6/2007 | Prisco et al. |
| 2007/0142971 | A1 | 6/2007 | Schena et al. |
| 2008/0103491 | A1 | 5/2008 | Omori et al. |
| 2008/0140088 | A1 | 6/2008 | Orban, III |
| 2009/0248038 | A1 | 10/2009 | Blumenkranz et al. |
| 2009/0248039 | A1 | 10/2009 | Cooper et al. |
| 2010/0152566 | A1 | 6/2010 | Rains et al. |
| 2010/0163057 | A1 | 7/2010 | Anderson et al. |
| 2010/0170519 | A1 | 7/2010 | Romo et al. |
| 2010/0175701 | A1 | 7/2010 | Reis et al. |
| 2010/0234857 | A1 | 9/2010 | Itkowitz et al. |
| 2011/0015650 | A1 | 1/2011 | Choi et al. |
| 2011/0084113 | A1 | 4/2011 | Bedi et al. |
| 2011/0118754 | A1 | 5/2011 | Dachs, II et al. |
| 2011/0213383 | A1 | 9/2011 | Lee et al. |
| 2011/0277776 | A1 | 11/2011 | McGrogan et al. |
| 2011/0288560 | A1 | 11/2011 | Shohat et al. |
| 2011/0290854 | A1 | 12/2011 | Timm et al. |
| 2011/0290855 | A1 | 12/2011 | Moore et al. |
| 2011/0295270 | A1 | 12/2011 | Giordano et al. |
| 2011/0313477 | A1 | 12/2011 | McLean et al. |
| 2012/0150192 | A1 | 6/2012 | Dachs, II et al. |
| 2012/0197094 | A1 | 8/2012 | Zhang et al. |
| 2012/0239060 | A1 | 9/2012 | Orban, III et al. |
| 2012/0247489 | A1 | 10/2012 | Orban, III et al. |
| 2012/0292367 | A1 | 11/2012 | Morgan et al. |
| 2013/0110129 | A1 | 5/2013 | Reid et al. |
| 2013/0211397 | A1 | 8/2013 | Parihar et al. |
| 2013/0211401 | A1 | 8/2013 | Bailey et al. |
| 2013/0274062 | A1 | 10/2013 | Arai et al. |
| 2013/0274657 | A1 | 10/2013 | Zirps et al. |
| 2013/0325034 | A1 | 12/2013 | Schena et al. |
| 2013/0331858 | A1 | 12/2013 | Devengenzo et al. |
| 2014/0000411 | A1 | 1/2014 | Shelton, IV et al. |
| 2014/0001234 | A1 | 1/2014 | Shelton, IV et al. |
| 2014/0001235 | A1 | 1/2014 | Shelton, IV |
| 2014/0007886 | A1 | 1/2014 | Singh et al. |
| 2014/0066944 | A1 | 3/2014 | Taylor et al. |
| 2014/0069437 | A1 | 3/2014 | Reis et al. |
| 2015/0223832 | A1 | 8/2015 | Swaney et al. |
| 2016/0184037 | A1 | 6/2016 | Cooper et al. |
| 2017/0172549 | A1 | 6/2017 | Smaby et al. |
| 2018/0168752 | A1 | 6/2018 | Scheib et al. |
| 2018/0344419 | A1 | 12/2018 | Dachs, II et al. |
| 2019/0183596 | A1 | 6/2019 | Dachs, II |
| 2019/0254766 | A1 | 8/2019 | Dachs, II |
| 2019/0365494 | A1 | 12/2019 | Dachs, II et al. |
| 2019/0380803 | A1 | 12/2019 | Dachs, II et al. |
| 2020/0069389 | A1 | 3/2020 | Morrissette et al. |
| 2020/0155130 | A1 | 5/2020 | Smaby et al. |
| 2020/0222139 | A1 | 7/2020 | Dachs et al. |
| 2020/0281677 | A1 | 9/2020 | Dachs et al. |
| 2021/0137627 | A1 | 5/2021 | Dachs, II et al. |
| 2021/0196420 | A1 | 7/2021 | Dachs, II et al. |
| 2022/0361975 | A1 | 11/2022 | Dachs, II |

FOREIGN PATENT DOCUMENTS

| | | | | |
|---|---|---|---|---|
| CN | 101297267 | A | | 10/2008 |
| CN | 101443162 | A | | 5/2009 |
| CN | 101454092 | A | | 6/2009 |
| CN | 102630154 | A | * 8/2012 | ............. A61B 17/00 |
| CN | 102711635 | A | | 10/2012 |

(56) References Cited

FOREIGN PATENT DOCUMENTS

| | | | |
|---|---|---|---|
| CN | 103038141 A | 4/2013 | |
| CN | 203234838 U | 10/2013 | |
| DE | 20015892 U1 | 1/2001 | |
| DE | 102012008535 A1 | 10/2013 | |
| DE | 102012013242 A1 | 1/2014 | |
| EP | 1815950 A1 | 8/2007 | |
| EP | 1862123 A2 | 12/2007 | |
| EP | 1897511 A2 | 3/2008 | |
| EP | 2259744 A1 | 12/2010 | |
| EP | 2691043 A1 | 2/2014 | |
| FR | 2895230 A1 * | 6/2007 | ............ A61B 17/00 |
| GB | 2538326 A | 11/2016 | |
| JP | H0666326 A | 3/1994 | |
| JP | H07163574 A | 6/1995 | |
| JP | 2001187067 A | 7/2001 | |
| JP | 2002500524 A | 1/2002 | |
| JP | 2003325543 A | 11/2003 | |
| JP | 2006511285 A | 4/2006 | |
| JP | 2010022415 A | 2/2010 | |
| JP | 2012050706 A | 3/2012 | |
| JP | 2012210294 A | 11/2012 | |
| JP | 2013502280 A | 1/2013 | |
| JP | 2013034833 A | 2/2013 | |
| JP | 2013034859 A | 2/2013 | |
| KR | 20080100212 A | 11/2008 | |
| KR | 20110032444 A | 3/2011 | |
| KR | 20110036452 A | 4/2011 | |
| KR | 20110095795 A | 8/2011 | |
| KR | 20130080638 A | 7/2013 | |
| KR | 20130120316 A | 11/2013 | |
| WO | WO-9825666 A1 | 6/1998 | |
| WO | WO-2004060184 A1 | 7/2004 | |
| WO | WO-2007075864 A1 | 7/2007 | |
| WO | WO-2007095637 A1 | 8/2007 | |
| WO | WO-2007111737 A2 | 10/2007 | |
| WO | WO-2007126443 A2 | 11/2007 | |
| WO | WO-2007142698 A2 | 12/2007 | |
| WO | WO-2008101228 A2 | 8/2008 | |
| WO | WO-2009123925 A1 | 10/2009 | |
| WO | WO-2009151205 A1 | 12/2009 | |
| WO | WO-2010126128 A1 | 11/2010 | |
| WO | WO-2010126129 A1 | 11/2010 | |
| WO | WO-2011037394 A2 | 3/2011 | |
| WO | WO-2011143016 A1 | 11/2011 | |
| WO | WO-2012158449 A1 * | 11/2012 | ............ A61B 17/00 |
| WO | WO-2013018931 A1 | 2/2013 | |
| WO | WO-2013181536 A1 | 12/2013 | |
| WO | WO-2014004255 A1 | 1/2014 | |
| WO | WO-2014005689 A2 | 1/2014 | |
| WO | WO-2014035308 A1 | 3/2014 | |
| WO | WO-2014035803 A1 | 3/2014 | |
| WO | WO-2015023730 A1 | 2/2015 | |
| WO | WO-2015142824 A1 | 9/2015 | |

OTHER PUBLICATIONS

Extended European Search Report for Application No. EP20154204.0, mailed on May 7, 2020, 7 pages.
Extended European Search Report for Application No. EP20154737.9, mailed on Apr. 17, 2020, 10 pages.
Extended European Search Report for Application No. EP20161337.9, mailed on May 7, 2020, 8 pages.
Extended European Search Report for Application No. EP20159147.6, mailed on Jun. 16, 2020, 7 pages.
Extended European Search Report for Application No. EP20172196.6 mailed on Aug. 7, 2020, 8 pages.
Extended European Search Report for Application No. EP22169553.9, mailed on Jul. 18, 2022, 09 pages.
Extended European Search Report for Application No. EP22179743.4, mailed on Sep. 2, 2022 7 pages.
Extended European Search Report for Application No. 15765493.0, mailed on Jul. 28, 2017, 7 pages.
Extended European Search Report for Application No. 15765779.2, mailed on Jul. 18, 2017, 8 pages.
Extended European Search Report for Application No. 15766019.2, mailed on Oct. 20, 2017, 7 pages.
Extended European Search Report for Application No. 19181058.9 mailed on Aug. 22, 2019, 7 pages.
Extended European Search Report for Application No. EP15764089.7, mailed on Oct. 25, 2017, 11 pages.
Extended European Search Report for Application No. EP15764268.7, mailed on Nov. 6, 2017, 8 pages.
Extended European Search Report for Application No. EP15764610.0, mailed on Nov. 23, 2017, 8 pages.
Extended European Search Report for Application No. EP15764745.4, mailed on Oct. 30, 2017, 10 pages.
Extended European Search Report for Application No. EP15764881.7, mailed on Nov. 30, 2017, 10 pages.
Extended European Search Report for Application No. EP15764940.1, mailed on Oct. 30, 2017, 8 pages.
International Search Report and Written Opinion for Application No. PCT/US15/20876, mailed on Jun. 12, 2015, 17 pages.
International Search Report and Written Opinion for Application No. PCT/US15/20880, mailed on Jul. 14, 2015, 9 pages.
International Search Report and Written Opinion for Application No. PCT/US15/20882, mailed on May 29, 2015, 14 pages.
International Search Report and Written Opinion for Application No. PCT/US15/20884, mailed on Jun. 12, 2015, 13 pages.
International Search Report and Written Opinion for Application No. PCT/US15/20885, mailed on Jun. 5, 2015, 7 pages.
International Search Report and Written Opinion for Application No. PCT/US15/20886, mailed on Jun. 4, 2015, 19 pages.
International Search Report and Written Opinion for Application No. PCT/US15/20888, mailed on Jun. 5, 2015, 9 pages.
International Search Report and Written Opinion for Application No. PCT/US15/21020, mailed on Jun. 5, 2015, 10 pages.
International Search Report and Written Opinion for Application No. PCT/US15/21111, mailed on May 21, 2015, 10 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

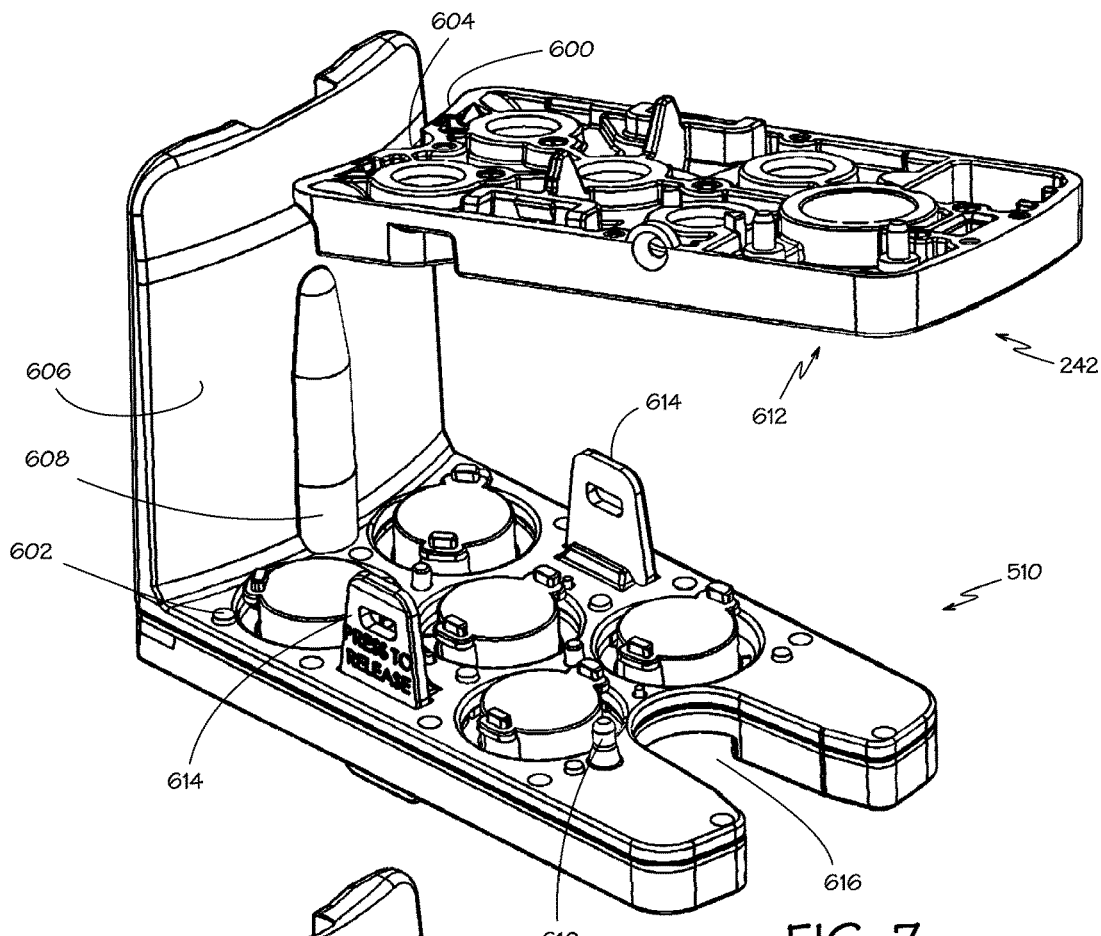
FIG. 7
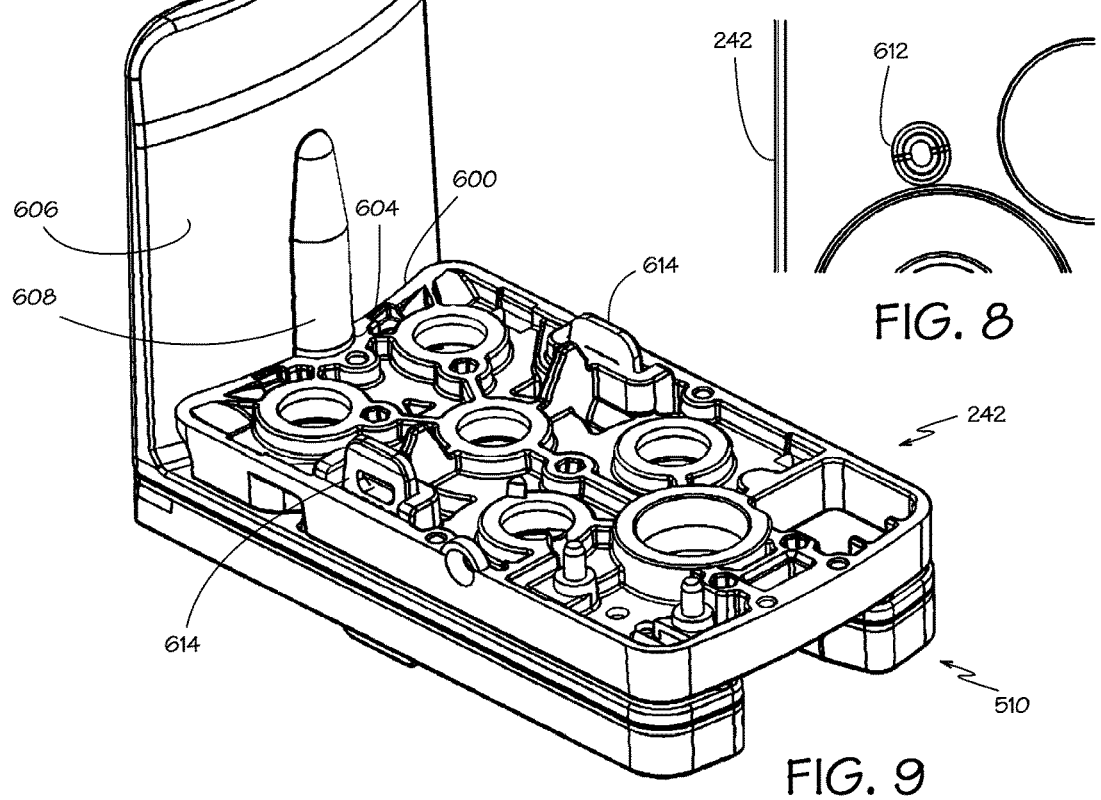
FIG. 8
FIG. 9

ALIGNMENT AND ENGAGEMENT FOR TELEOPERATED ACTUATED SURGICAL INSTRUMENT

This application is related to and claims priority to U.S. application Ser. No. 15/121,369 filed Aug. 24, 2016, entitled "Alignment and Engagement for Teleoperated Actuated Surgical Instrument", which is a National Stage Entry of PCT/US2015/020882 filed on Mar. 17, 2015, which claims benefit of the following provisional applications:

| U.S. | 62/104,306 | 16 Jan. 2015 (16 Jan. 2015) |
|---|---|---|
| U.S. | 62/103,991 | 15 Jan. 2015 (15 Jan. 2015) |
| U.S. | 62/019,318 | 30 Jun. 2014 (30 Jun. 2014) |
| U.S. | 61/954,571 | 17 Mar. 2014 (17 Mar. 2014) |
| U.S. | 61/954,557 | 17 Mar. 2014 (17 Mar. 2014) |
| U.S. | 61/954,502 | 17 Mar. 2014 (17 Mar. 2014) |
| U.S. | 61/954,497 | 17 Mar. 2014 (17 Mar. 2014) |
| U.S. | 61/954,595 | 17 Mar. 2014 (17 Mar. 2014) |

Each of these applications is specifically incorporated herein by reference in their entirety and for all purposes.

FIELD

Embodiments of the invention relate to the field of field of alignment guides; and more specifically, to alignment guides for attaching surgical instruments to teleoperated actuators.

BACKGROUND

Minimally invasive medical techniques have been used to reduce the amount of extraneous tissue which may be damaged during diagnostic or surgical procedures, thereby reducing patient recovery time, discomfort, and deleterious side effects. Traditional forms of minimally invasive surgery include endoscopy. One of the more common forms of endoscopy is laparoscopy, which is minimally invasive inspection or surgery within the abdominal cavity. In traditional laparoscopic surgery, a patient's abdominal cavity is insufflated with gas, and cannula sleeves are passed through small (approximately 12 mm) incisions in the musculature of the patient's abdomen to provide entry ports through which laparoscopic surgical instruments can be passed in a sealed fashion.

The laparoscopic surgical instruments generally include a laparoscope for viewing the surgical field and surgical instruments having end effectors. Typical surgical end effectors include clamps, graspers, scissors, staplers, and needle holders, for example. The surgical instruments are similar to those used in conventional (open) surgery, except that the working end or end effector of each surgical instrument is separated from its handle by an approximately 30 cm. long extension tube, for example, so as to permit the operator to introduce the end effector to the surgical site and to control movement of the end effector relative to the surgical site from outside a patient's body.

In order to provide improved control of the working tools, it may be desirable to control the surgical instrument with teleoperated actuators. The surgeon may operate controls on a console to indirectly manipulate the instrument that is connected to the teleoperated actuators. The surgical instrument is detachably coupled to the teleoperated actuators so that the surgical instrument can be separately sterilized and selected for use as needed instrument for the surgical procedure to be performed. The surgical instrument may be changed during the course of a surgery.

Performing surgery with teleoperated surgical instruments creates new challenges. One challenge is the need to maintain the region adjacent the patient in a sterile condition. However, the motors, sensors, encoders and electrical connections that are necessary to control the surgical instruments typically cannot be sterilized using conventional methods, e.g., steam, heat and pressure or chemicals, because they would be damaged or destroyed in the sterilization process.

Another challenge with teleoperated surgery systems is that a number of connections are required between the surgical instrument and the teleoperated actuator and its controller. Connections are required to transmit the actuator forces, electrical signals, and data. This makes the attachment of the surgical instrument to the teleoperated actuator and its controller complex.

It would be desirable to provide an easier and more effective way to engage and disengage a surgical instrument and a teleoperated actuator drive while preventing contamination of the teleoperated actuator and allowing quick and reliable attachment of a succession of surgical instruments that maintains a sterile area around the surgical instrument.

SUMMARY

An instrument sterile adapter for coupling a surgical instrument and an instrument carriage includes an adapter control surface that extends control features of a control surface of the instrument carriage and receives an instrument control surface of the surgical instrument. A shaft receiving slot is positioned in the adapter control surface to receive an elongate tube of the surgical instrument when the adapter control surface receives the instrument control surface of the surgical instrument. The elongate tube may couple a proximal control mechanism of the surgical instrument to an end effector. The instrument sterile adapter may include a convex curved surface substantially perpendicular to and facing the adapter control surface to receive a corresponding concave curved surface on the instrument control surface. A bullet portion on the convex curved surface may engage a bullet receiving feature in the corresponding concave curved surface on the instrument control surface.

Other features and advantages of the present invention will be apparent from the accompanying drawings and from the detailed description that follows below.

BRIEF DESCRIPTION OF THE DRAWINGS

The invention may best be understood by referring to the following description and accompanying drawings that are used to illustrate embodiments of the invention by way of example and not limitation. In the drawings, in which like reference numerals indicate similar elements:

FIG. 7 is a perspective view of the instrument control surface.

FIG. 8 is a plan view of a portion of the instrument control surface.

FIG. 9 is a perspective view of the instrument control surface.

DESCRIPTION OF EMBODIMENTS

Figure 1:
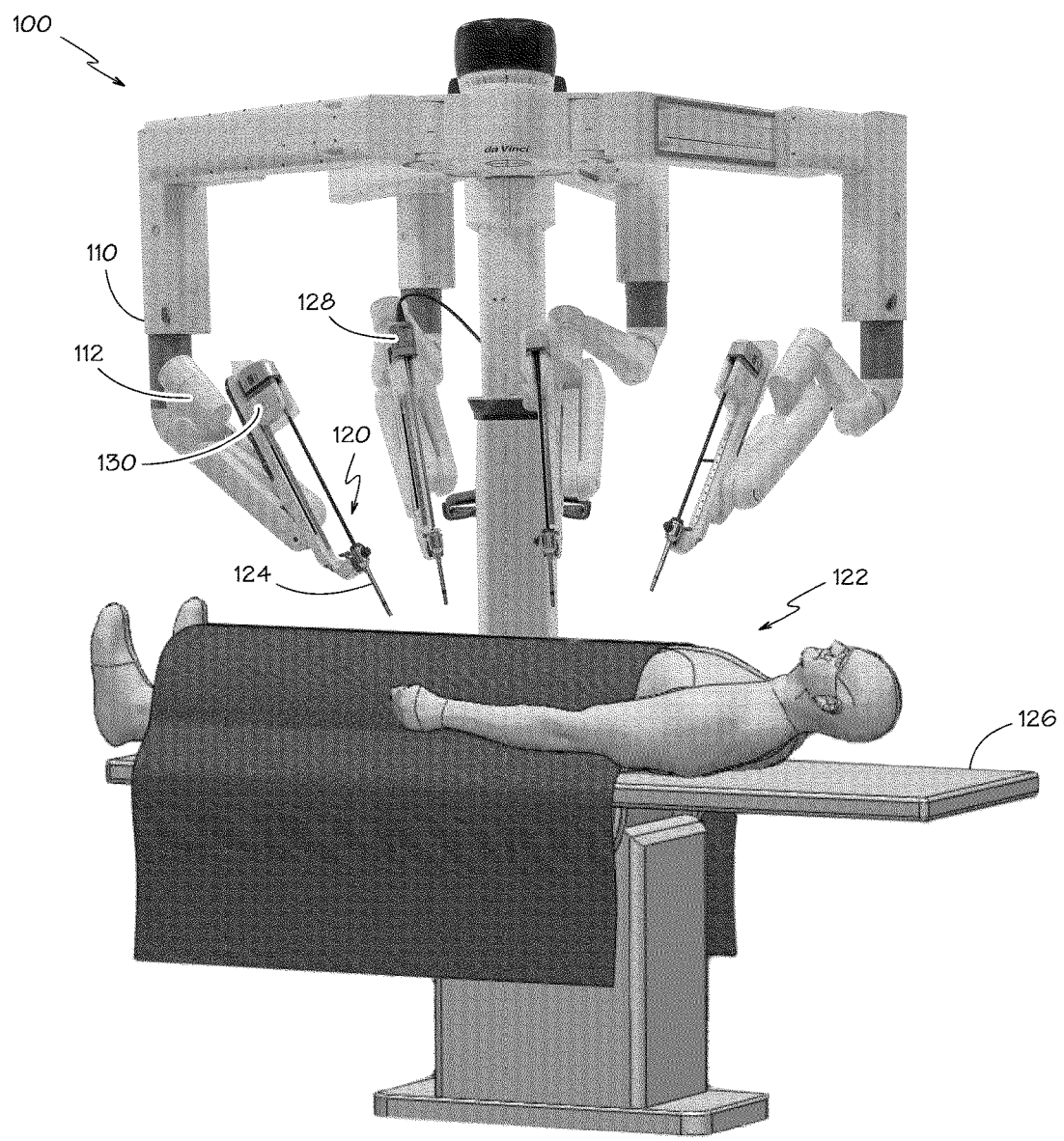
FIG. 1 is a view of an illustrative patient-side portion of a teleoperated surgical system.

In the following description, numerous specific details are set forth. However, it is understood that embodiments of the invention may be practiced without these specific details. In other instances, well-known circuits, structures and techniques have not been shown in detail in order not to obscure the understanding of this description.

In the following description, reference is made to the accompanying drawings, which illustrate several embodiments of the present invention. It is understood that other embodiments may be utilized, and mechanical compositional, structural, electrical, and operational changes may be made without departing from the spirit and scope of the present disclosure. The following detailed description is not to be taken in a limiting sense, and the scope of the embodiments of the present invention is defined only by the claims of the issued patent.

The terminology used herein is for the purpose of describing particular embodiments only and is not intended to be limiting of the invention. Spatially relative terms, such as "beneath", "below", "lower", "above", "upper", and the like may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (e.g., rotated 90 degrees or at other orientations) and the spatially relative descriptors used herein interpreted accordingly.

As used herein, the singular forms "a", "an", and "the" are intended to include the plural forms as well, unless the context indicates otherwise. It will be further understood that the terms "comprises" and/or "comprising" specify the presence of stated features, steps, operations, elements, and/or components, but do not preclude the presence or addition of one or more other features, steps, operations, elements, components, and/or groups thereof.

The term "object" generally refers to a component or group of components. For example, an object may refer to either a pocket or a boss of a disk within the specification or claims. Throughout the specification and claims, the terms "object," "component," "portion," "part" and "piece" are used interchangeably.

The terms "instrument" and "surgical instrument" are used herein to describe a medical device configured to be inserted into a patient's body and used to carry out surgical or diagnostic procedures. The instrument includes an end effector. The end effector may be a surgical tool associated with one or more surgical tasks, such as a forceps, a needle driver, a shears, a bipolar cauterizer, a tissue stabilizer or retractor, a clip applier, an anastomosis device, an imaging device (e.g., an endoscope or ultrasound probe), and the like. Some instruments used with embodiments of the invention further provide an articulated support (sometimes referred to as a "wrist") for the surgical tool so that the position and orientation of the surgical tool can be manipulated with one or more mechanical degrees of freedom in relation to the instrument's shaft. Further, many surgical end effectors include a functional mechanical degree of freedom, such as jaws that open or close, or a knife that translates along a path. Surgical instruments may also contain stored (e.g., on a semiconductor memory inside the instrument) information that may be permanent or may be updatable by the surgical system. Accordingly, the system may provide for either one-way or two-way information communication between the instrument and one or more system components.

The terms "or" and "and/or" as used herein are to be interpreted as inclusive or meaning any one or any combination. Therefore, "A, B or C" or "A, B and/or C" mean "any of the following: A; B; C; A and B; A and C; B and C; A, B and C." An exception to this definition will occur only when a combination of elements, functions, steps or acts are in some way inherently mutually exclusive.

FIG. 1 is a view of an illustrative patient-side portion 100 of a teleoperated surgical system, in accordance with embodiments of the present invention. The patient-side portion 100 includes support assemblies 110 and one or more surgical instrument manipulators 112 at the end of each support assembly. The support assemblies optionally include one or more unpowered, lockable setup joints that are used to position the surgical instrument manipulator(s) 112 with reference to the patient for surgery. As depicted, the patient-side portion 100 rests on the floor. In other embodiments the patient-side portion may be mounted to a wall, to the ceiling, to the operating table 126, which also supports the patient's body 122, or to other operating room equipment. Further, while the patient-side portion 100 is shown as including four manipulators 112, more or fewer manipulators 112 may be used. Still further, the patient-side portion 100 may consist of a single assembly as shown, or it may include two or more separate assemblies, each optionally mounted in various possible ways.

Each surgical instrument manipulator 112 supports one or more surgical instruments 120 that operate at a surgical site within the patient's body 122. Each manipulator 112 may be provided in a variety of forms that allow the associated surgical instrument to move with one or more mechanical degrees of freedom (e.g., all six Cartesian degrees of freedom, five or fewer Cartesian degrees of freedom, etc.). Typically, mechanical or control constraints restrict each manipulator 112 to move its associated surgical instrument around a center of motion on the instrument that stays stationary with reference to the patient, and this center of motion is typically located to be at the position where the instrument enters the body.

A functional teleoperated surgical system will generally include a vision system portion (not shown) that enables the operator to view the surgical site from outside the patient's body 122. The vision system typically includes a surgical instrument that has a video-image-capture function 128 (a "camera instrument") and one or more video displays for displaying the captured images. In some surgical system configurations, the camera instrument 128 includes optics that transfer the images from the distal end of the camera instrument 128 to one or more imaging sensors (e.g., CCD or CMOS sensors) outside of the patient's body 122. Alternatively, the imaging sensor(s) may be positioned at the distal end of the camera instrument 128, and the signals produced by the sensor(s) may be transmitted along a lead or wirelessly for processing and display on the video display. An illustrative video display is the stereoscopic display on the surgeon's console in surgical systems commercialized by Intuitive Surgical, Inc., Sunnyvale, California.

A functional teleoperated surgical system will further include a control system portion (not shown) for controlling the movement of the surgical instruments 120 while the instruments are inside the patient. The control system portion may be at a single location in the surgical system, or it may be distributed at two or more locations in the system (e.g., control system portion components may be in the system's patient-side portion 100, in a dedicated system control console, or in a separate equipment rack). The teleoperated master/slave control may be done in a variety of ways, depending on the degree of control desired, the size of the surgical assembly being controlled, and other factors. In some embodiments, the control system portion includes one or more manually-operated input devices, such as a joystick, exoskeletal glove, a powered and gravity-compensated manipulator, or the like. These input devices control teleoperated motors which, in turn, control the movement of the surgical instrument.

The forces generated by the teleoperated motors are transferred via drivetrain mechanisms, which transmit the forces from the teleoperated motors to the surgical instrument 120. In some telesurgical embodiments, the input devices that control the manipulator(s) may be provided at a location remote from the patient, either inside or outside the room in which the patient is placed. The input signals from the input devices are then transmitted to the control system portion. Persons familiar with telemanipulative, teleoperative, and telepresence surgery will know of such systems and their components, such as the da Vinci® Surgical System commercialized by Intuitive Surgical, Inc. and the Zeus® Surgical System originally manufactured by Computer Motion, Inc., and various illustrative components of such systems.

As shown, both the surgical instrument 120 and an optional entry guide 124 (e.g., a cannula in the patient's abdomen) are removably coupled to the distal end of a manipulator 112, with the surgical instrument 120 inserted through the entry guide 124. Teleoperated actuators in the manipulator 112 move the surgical instrument 120 as a whole. The manipulator 112 further includes an instrument carriage 130. The surgical instrument 120 is detachably connected to the carriage 130. The teleoperated actuators housed in the carriage 130 provide a number of controller motions which the surgical instrument 120 translates into a variety of movements of the end effector on the surgical instrument. Thus the teleoperated actuators in the carriage 130 move only one or more components of the surgical instrument 120 rather than the instrument as a whole. Inputs to control either the instrument as a whole or the instrument's components are such that the input provided by a surgeon to the control system portion (a "master" command) is translated into a corresponding action by the surgical instrument (a "slave" response).

Figure 2:
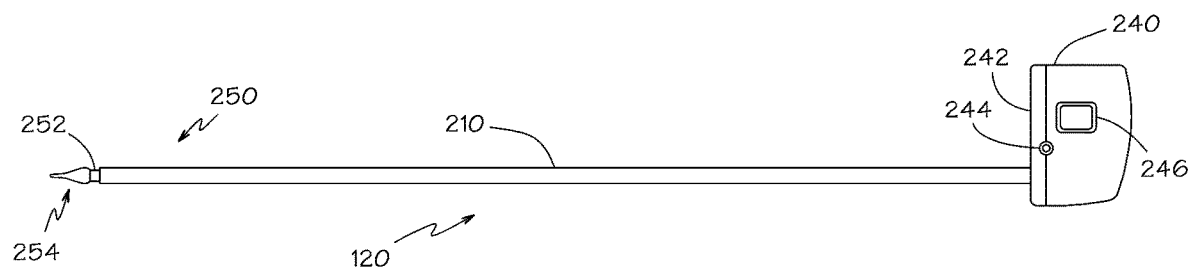
FIG. 2 is a side view of a surgical instrument for use with a teleoperated actuator.

FIG. 2 is a side view of an illustrative embodiment of the surgical instrument 120, comprising a distal portion 250 and a proximal control mechanism 240 coupled by an elongate tube 210. The distal portion 250 of the surgical instrument 120 may provide any of a variety of end effectors such as the forceps 254 shown, a needle driver, a cautery device, a cutting tool, an imaging device (e.g., an endoscope or ultrasound probe), or a combined device that includes a combination of two or more various tools and imaging devices. In the embodiment shown, the end effector 254 is coupled to the elongate tube 210 by a "wrist" 252 that allows the orientation of the end effector to be manipulated with reference to the instrument tube 210.

Surgical instruments that are used with the invention may control their end effectors (surgical tools) with a plurality of rods and/or flexible cables. Rods, which may be in the form of tubes, may be combined with cables to provide a "push/pull" control of the end effector with the cables providing flexible sections as required. A typical elongate tube 210 for a surgical instrument 120 is small, perhaps five to eight millimeters in diameter, roughly the diameter of a large soda straw. The diminutive scale of the mechanisms in the surgical instrument 120 creates unique mechanical conditions and issues with the construction of these mechanisms that are unlike those found in similar mechanisms constructed at a larger scale, because forces and strengths of materials do not scale at the same rate as the size of the mechanisms. The cables must fit within the elongate tube 210 and be able to bend as they pass through the wrist joint 252.

In order to provide a sterile operation area while using a functional teleoperated surgical system, it is preferred that a barrier be placed between the non-sterile system and the sterile surgical field. Therefore, a sterile component, such as an instrument sterile adapter (ISA), is placed between the surgical instrument 120 and the teleoperated surgical instrument manipulator 130. The placement of an instrument sterile adapter between the surgical instrument 120 and the surgical instrument manipulator 130 includes the benefit of ensuring a sterile coupling point for the surgical instrument 120 and the surgical instrument manipulator 130. This permits removal of surgical instruments from the surgical instrument manipulator 130 and exchange with other surgical instruments during the course of a surgery.

Figure 3:
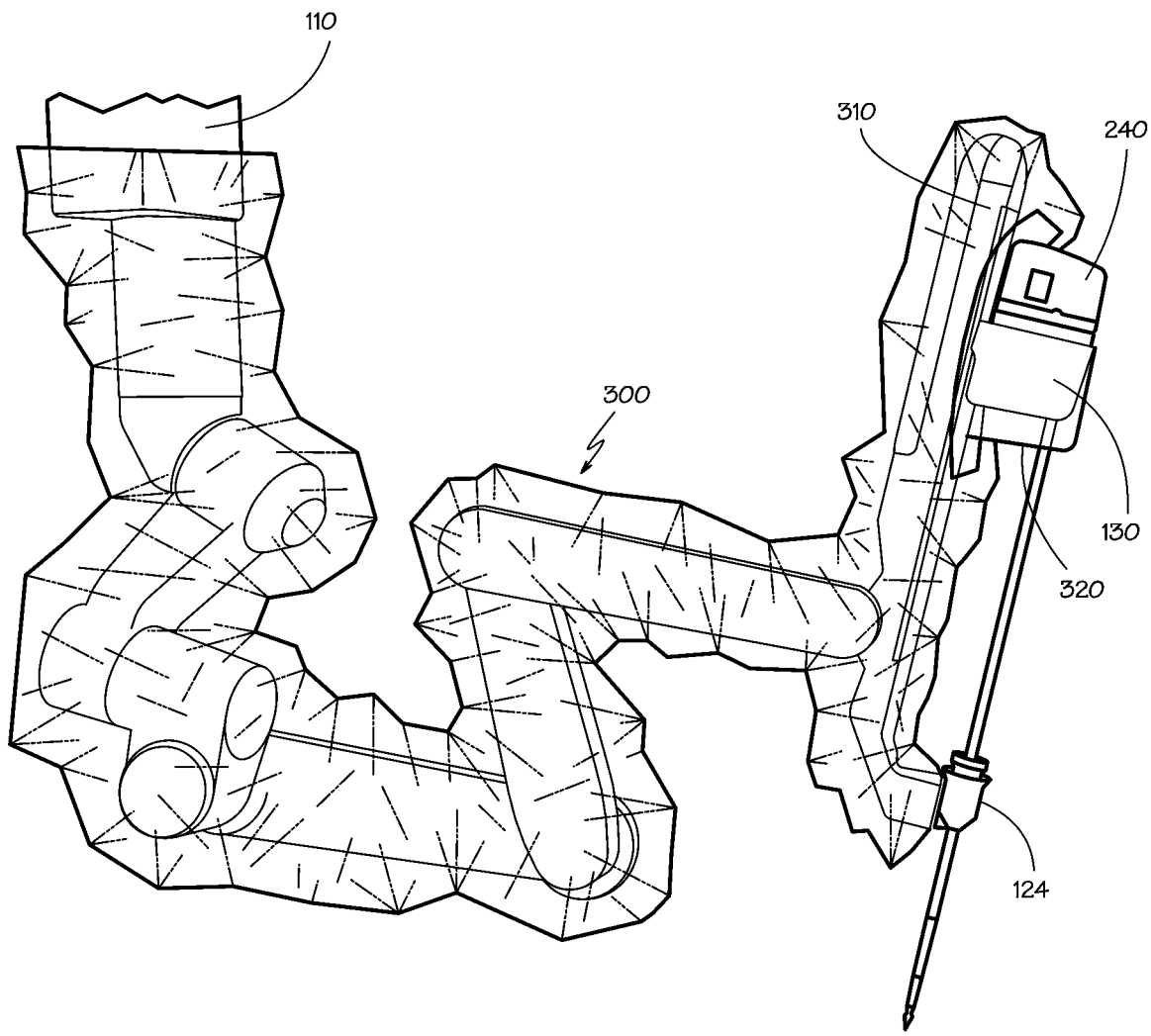
FIG. 3 is a perspective view of an instrument sterile adapter (ISA).

FIG. 3 is a perspective view of a setup joint that supports the carriage 130 which in turn supports the surgical instrument 120 on a strut 310. In preparation for surgery, the setup joint is covered with a sterile drape 300. The sterile drape protects the setup joint from contamination and provides a sterile surface around the setup joint. The majority of the sterile drape 300 is a plastic sheet, which may be in the form of a tube or bag, that covers the arms of the setup joint. For example, a single layer thermoplastic polyurethane (TPU) may be used. A lubricant may be included to reduce the tackiness of the plastic. The sheet may be about 100 micrometers (0.004 inch) thick. Other suitable materials may be used for the sheet.

Figure 4:
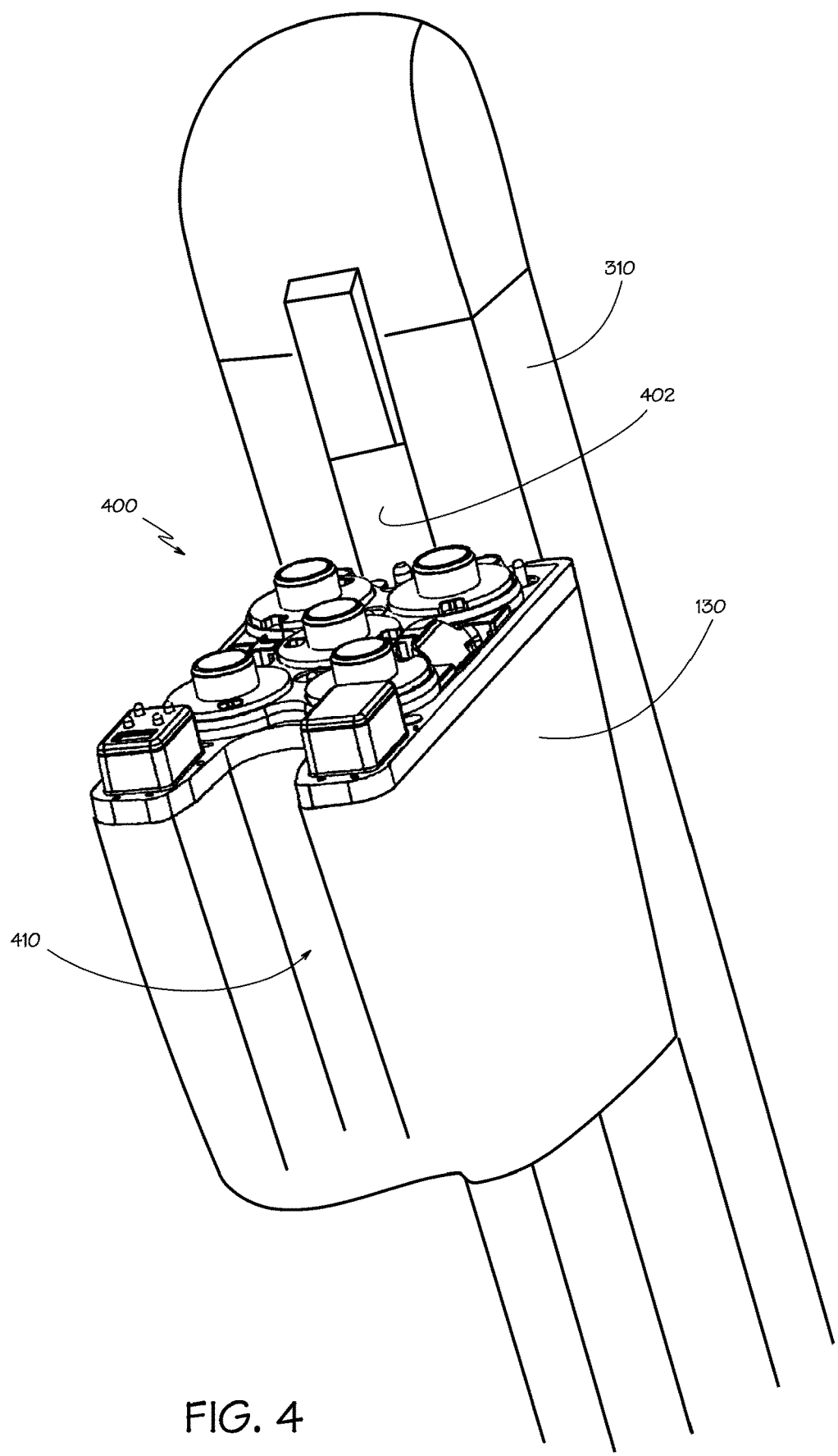
FIG. 4 is a top perspective view of a latch plate.

FIG. 4 is a perspective view of the strut 310 portion of the setup joint that supports the carriage 130. The sterile drape is not shown to allow the carriage 130 to be seen more clearly. One surface 400 of the carriage provides a number of mechanical and electrical interfaces to communicate mechanical motion and data signals between the control system, the teleoperated actuators, and the surgical instrument. It will be appreciated that the connections to the surgical instrument may require a penetration through the sterile drape. It is difficult to provide a penetration through the plastic sheet that is compatible with the connections between the carriage 130 and a surgical instrument. Further, the carriage 130 is shaped to allow the elongate tube 210 (FIG. 2) of the surgical instrument 120 to pass through an indentation 410 along one side of the carriage. It is difficult to drape the carriage with the plastic sheet due to the shape of the carriage.

Figure 5:
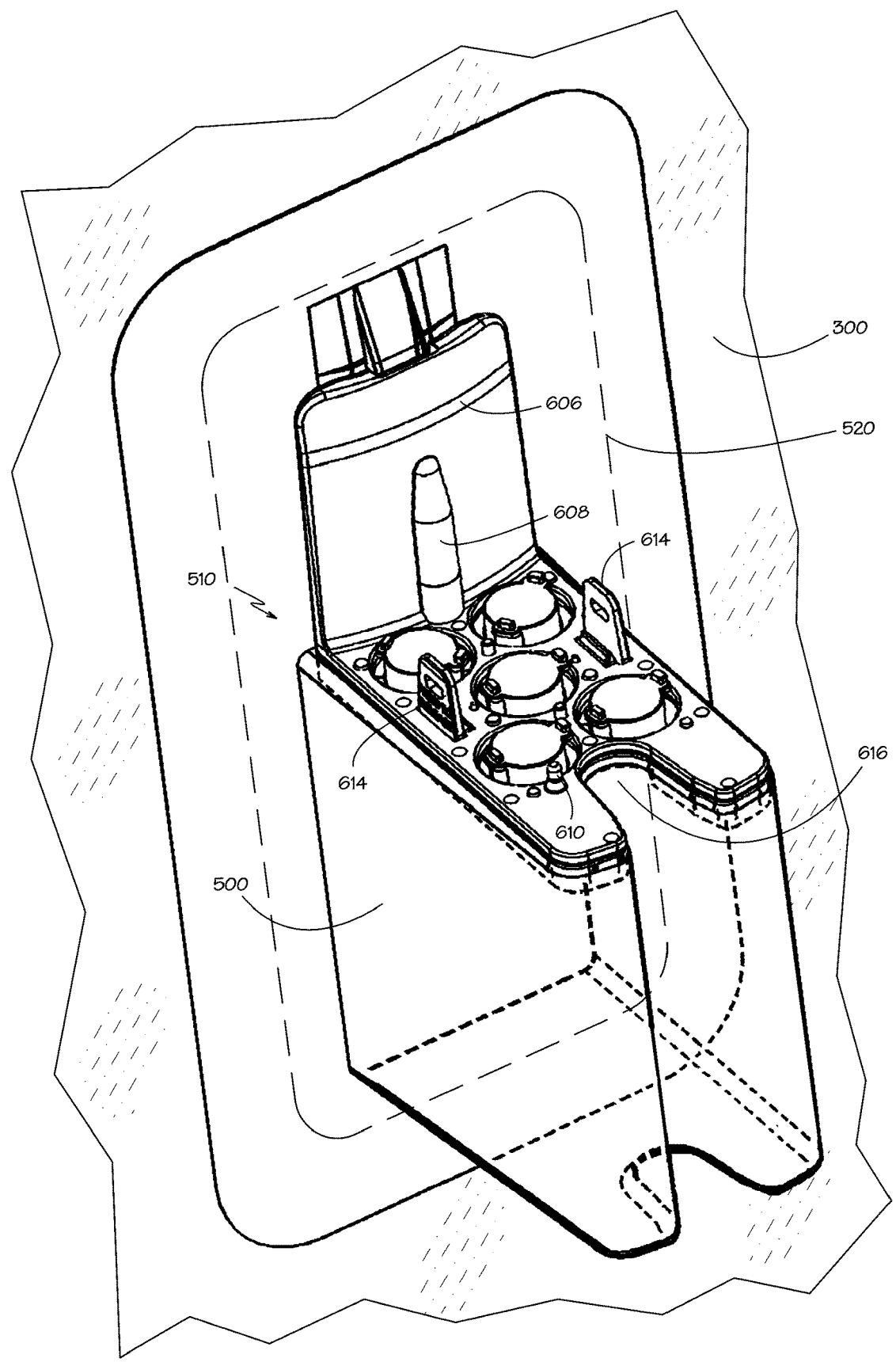
FIG. 5 is a bottom perspective view of a latch plate.

FIG. 5 is a perspective view of the portion of the sterile drape that is constructed to be placed around the carriage 130. The sterile drape includes three portions. The first portion is the plastic sheet 300 described above. The second portion is a pouch 500 shaped to fit around the carriage 130. The third portion is a largely rigid instrument sterile adapter (ISA) 510 that engages the control features 400 of the carriage 130 and provides a sterile counterpart of the control features for connection to a surgical instrument. The sterile drape is a disposable assembly.

The pouch 500 may be made from a material such as a cast urethane. The pouch 500 may be flexible but it should return to its original shape when not subject to stress. The pouch provides a portion of the drape that is a loose form fit around the carriage 130 to provide a clear work space for the teleoperated actuators and the surgical instrument.

An aperture 520 is formed in the plastic sheet 300 where the pouch 500 is joined to the plastic sheet. The plastic sheet may be joined to the pouch by any process that is compatible with the materials of the sheet and the pouch, such as by heat welding.

Figure 6:
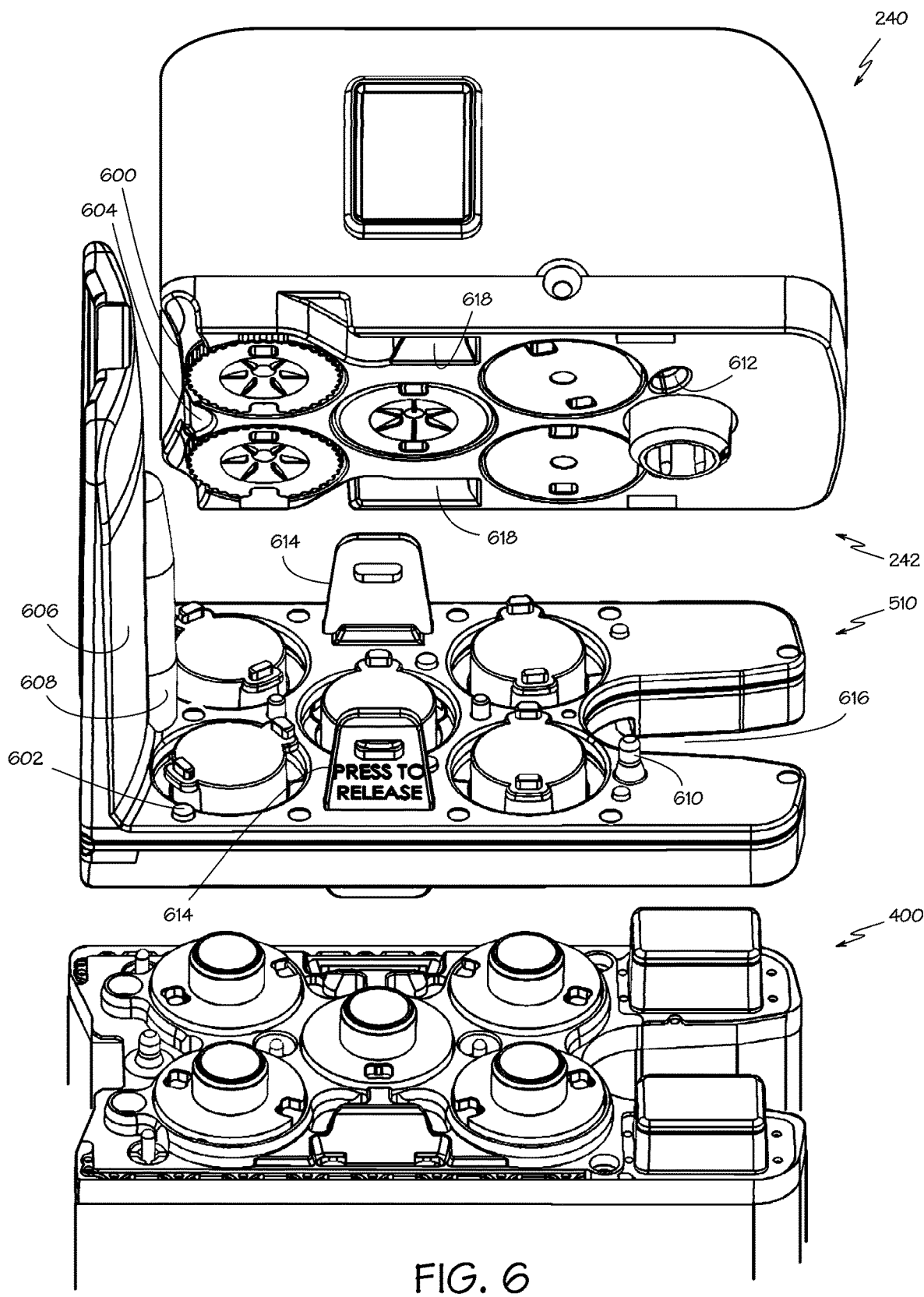
FIG. 6 is an elevation view of a latch plate.

FIG. 6 is a perspective view of the control surface 400 of the carriage, the ISA 510, and proximal control 240 of a surgical instrument that has been rotated to show the instrument control surface 242. The ISA 510 is coupled to the control surface 400 of the carriage as suggested by the figure. The ISA 510 provides an adapter control surface that extends the control features of the control surface 400 of the carriage 130 as a sterile, disposable surface that can receive the proximal control 240 of the teleoperated actuated surgical instrument 120 and engage the control features of the instrument control surface 242.

The ISA 510 includes a curved surface 606 that receives a corresponding curved surface 600 on the instrument control surface 242 as the instrument is being placed on the ISA. The curved surface 606 of the ISA is substantially perpendicular direction to the adapter control surface. The curved surfaces 600, 606 work in concert with the instrument shaft 210 location in the entry guide 124 and a shaft receiving slot 616 in the ISA to locate the instrument roughly in the plane parallel to the control surface of the ISA. The entry guide 124 constrains the instrument shaft 210 to rotation around a cylindrical axis of the instrument shaft and axial translation along the cylindrical axis of the instrument shaft. The curved surfaces 600, 606 of the ISA and the instrument control surface 242 tend to constrain the instrument control surface to rotation about the cylindrical axis of the ISA curved surface 606 and translation along the ISA curved surface. Since the cylindrical axis of the instrument shaft and the cylindrical axis of the ISA curved surface are spaced apart, they provide an effective constraint on the position of the instrument control surface.

Further insertion of the instrument shaft 210 into the entry guide 124 causes the instrument's bullet receiving feature 604 to engage the bullet portion 608 of the ISA curved surface 606. This combination more tightly constrains the instrument movements.

As the instrument control surface 242 approaches the ISA, latch arms 614 on the ISA enter latch receptacles 618 on the surgical instrument's proximal control 240. The latch receptacles 618 may provide a sloped surface to further aid in positioning the instrument control surface 242. It will be appreciated that the latch arms 614 are movable and that their positioning function is secondary to their primary latching function.

When the instrument is fully installed onto the ISA control surface, a locating pin 610 on the ISA enters a locating slot 612 on the instrument control surface 242 to tightly constrain movement of the proximal control 240 in the plane of the instrument control surface 242. The proximal control 240 is further constrained by the landing pads 602 on the ISA that support the control surface 242 of the instrument. When the proximal control 240 is latched to the ISA, the landing pads 602 on the ISA tightly constrain movement of the proximal control 240 perpendicular to the plane of the instrument control surface 242.

FIG. 7 is a perspective view of the instrument control surface 242 at the start of the installation onto the ISA 510. The curved surface 600 on the instrument control surface 242 is shown as it engages the corresponding curved surface 606 on the ISA 510. The remainder of the surgical instrument's proximal control is not shown to allow the curved surface 600 on the instrument control surface 242 to be seen more clearly.

FIG. 8 is a plan view of a portion of the instrument control surface 242 showing the locating slot 612 that receives the locating pin 610. The lower end of the bullet portion 608 acts somewhat like a pin in a hole although being a half-pin in a half-hole it cannot completely constrain the position of instrument control surface 242. The bullet portion 608 works with the locating pin 610 and locating slot 612 to control the tendency of the instrument control surface 242 to rotate in reaction to the applied rotary control torques. The locating slot 612 is only extended lengthwise by a small amount to compensate for the lack of control by the bullet feature. In another embodiment, not shown, the locating pin is on the instrument control surface and the locating slot is on the ISA.

FIG. 9 is a perspective view of the instrument control surface 242 fully installed onto the ISA 510.

Figure 10:
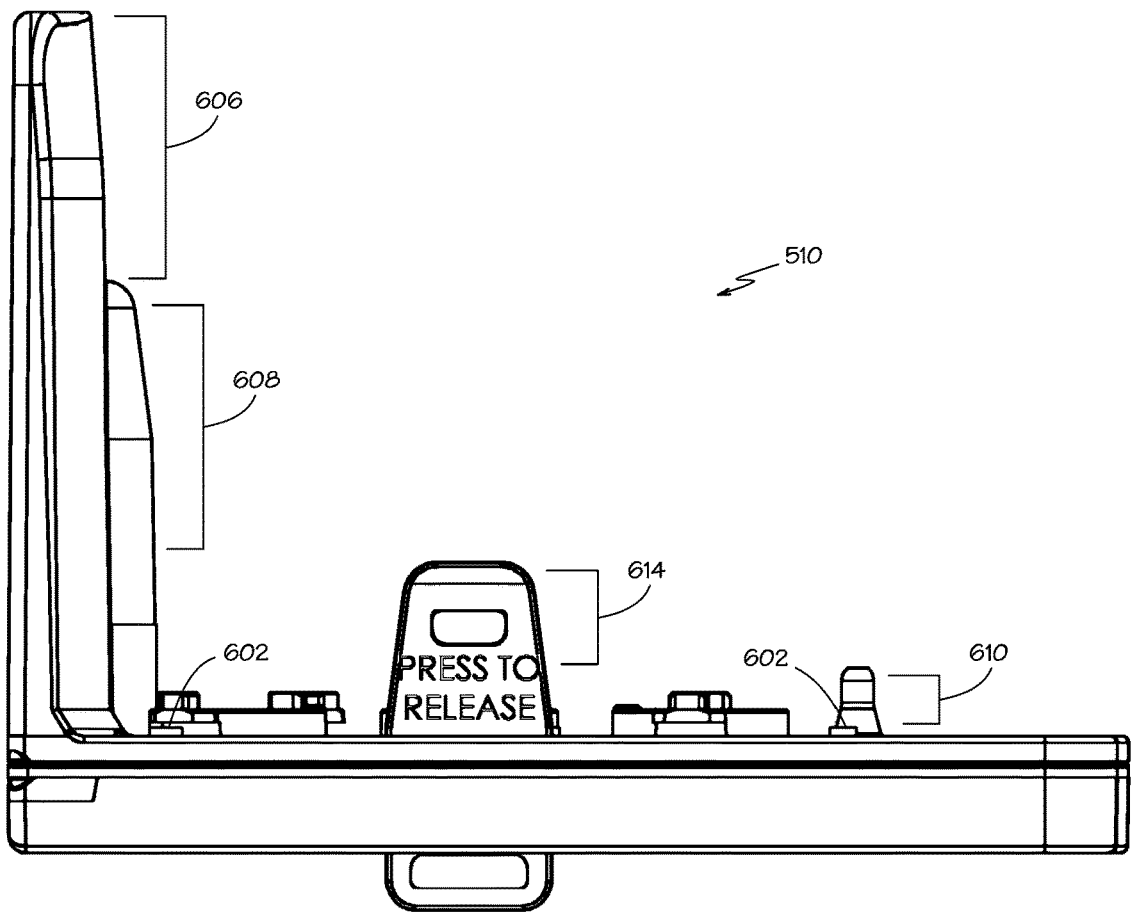
FIG. 10 is a side view of the ISA.

FIG. 10 is a side view of the ISA 510. It will be seen that the curved surface 606 on the ISA 510 provides a locating surface when the instrument control surface first engages the ISA. The bullet portion 608 provides a locating surface when the instrument control surface is moved closer to the ISA. The latch arms 614 contribute to the positioning of the instrument control surface as it moves still closer to the ISA. The locating pin 610 engages the instrument control surface and provides the final positioning and constraint of the instrument control surface 242 as the lower surface reaches the landing pads 602.

Figure 11:
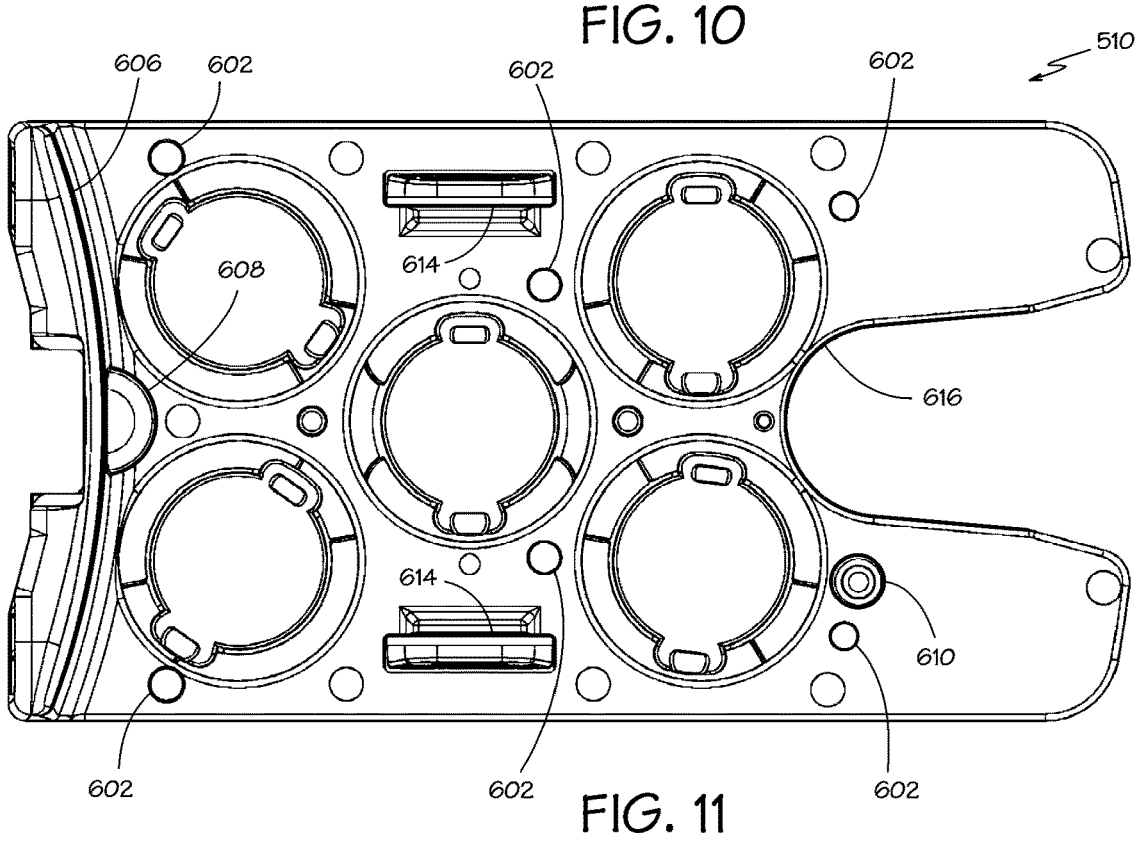
FIG. 11 is a top view of the ISA.

FIG. 11 is a top view of the ISA 510. The control surfaces—the landing pads 602, the curved surface 606, the bullet portion 608, the locating pin 610, the latch arms 614, and the shaft receiving slot 616—have been highlighted with heavier lines.

FIGS. 12-15 show the control surfaces of the ISA 510 and the corresponding control surfaces of the instrument control surface 242 in various stages of engagement.

Figure 12:
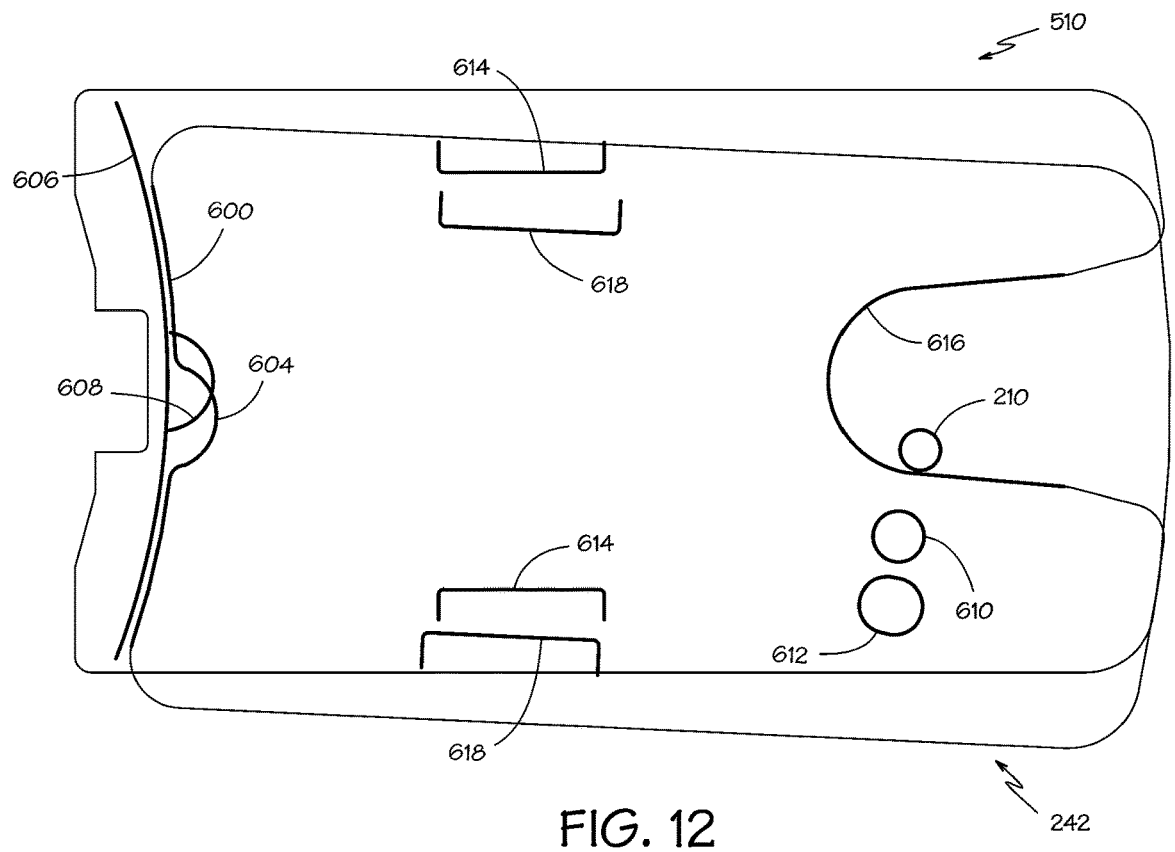
FIGS. 12-15 show the control surfaces of the ISA and the corresponding control surfaces of the instrument control surface in various stages of engagement.

FIG. 12 shows the initial engagement of the instrument control surface 242 with the ISA 510. The position of the instrument control surface 242 is constrained by the engagement of the curved surface 600 on the instrument control surface 242 with the corresponding curved surface 606 on the ISA 510 and by the instrument shaft 210 in the instrument guide (not shown) and the shaft receiving slot 616. As can be seen, the instrument control surface 242 is only loosely constrained during the initial engagement. This allows the surgical instrument to be easily engaged with the ISA to start the process of bringing the surgical instrument into an accurately positioned latched engagement with the ISA. It will be appreciated that the surgical draping associated with the ISA and other visual obstacles may require attaching the surgical instrument to the ISA with little or no view of the surfaces being engaged.

Figure 13:
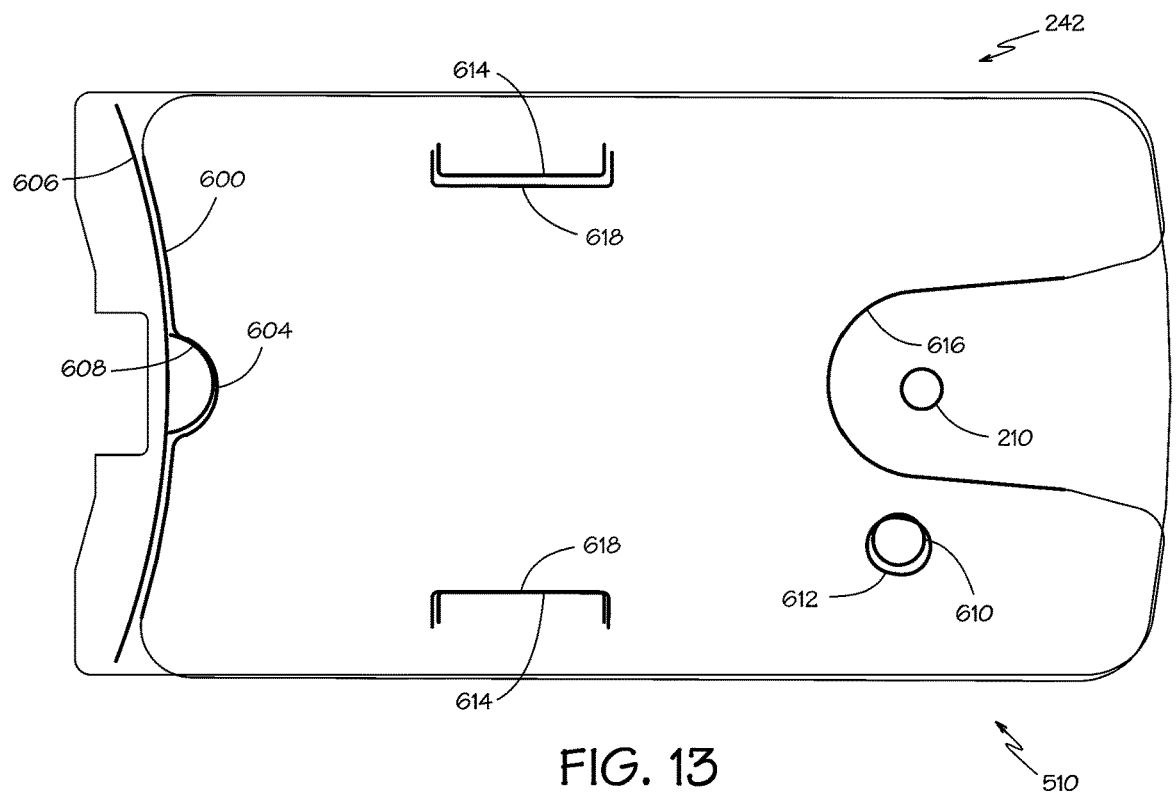

FIG. 13 shows the instrument control surface 242 when the bullet receiving feature 604 on the instrument control surface 242 engages the bullet portion 608 on the ISA 510. As can be seen, engaging the bullet portion 608 greatly increases the constraint on the position of the instrument control surface 242. The leading portion of the bullet portion 608 is tapered to aid in engaging the bullet portion. But the engagement of the curved surface 600 on the instrument control surface 242 with the corresponding curved surface 606 on the ISA 510 allows the instrument control surface to be moved along a controlled path that assists with engaging the bullet portion 608 even if the bullet receiving feature 604 is not initially aligned with the leading portion of the bullet portion.

Figure 14:
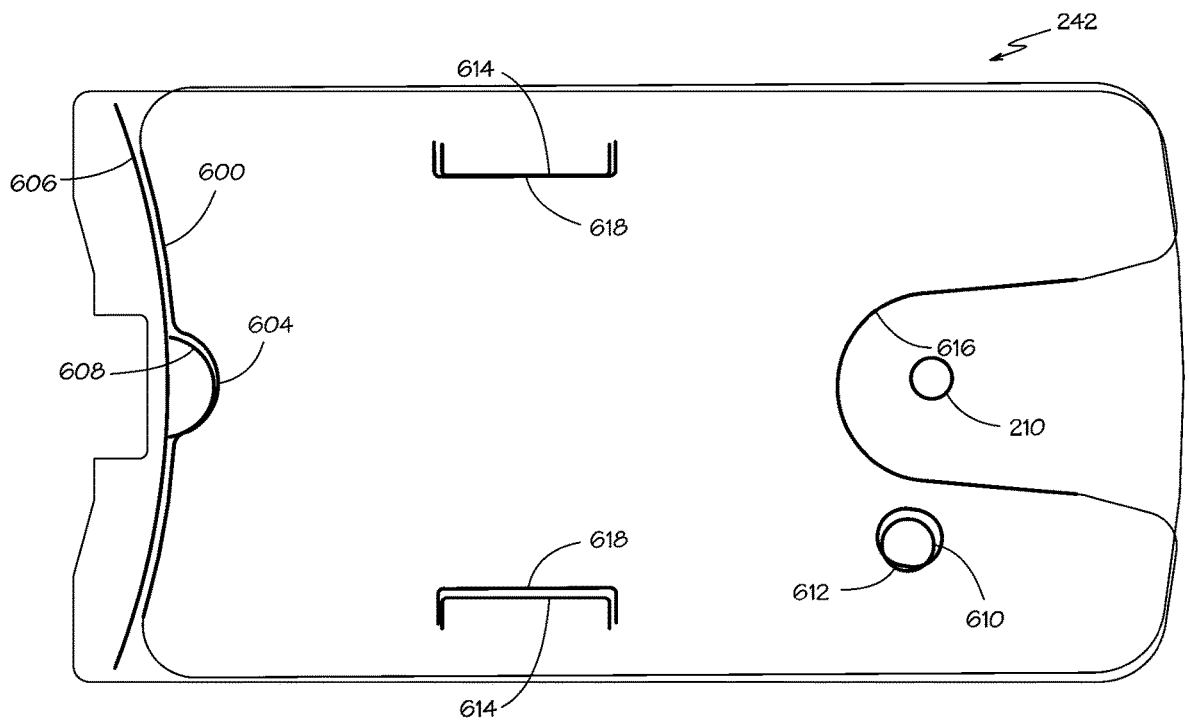

FIG. 14 shows the instrument control surface 242 when the latch arms 614 on the ISA 510 enter the latch receptacles 618 on the instrument control surface. While the engagement of the bullet portion 608 largely aligns the instrument control surface 242 so the latch arms 614 can readily enter the latch receptacles 618, the latch receptacles may be shaped so that engaging the latch arms further positions the instrument control surface.

Figure 15:
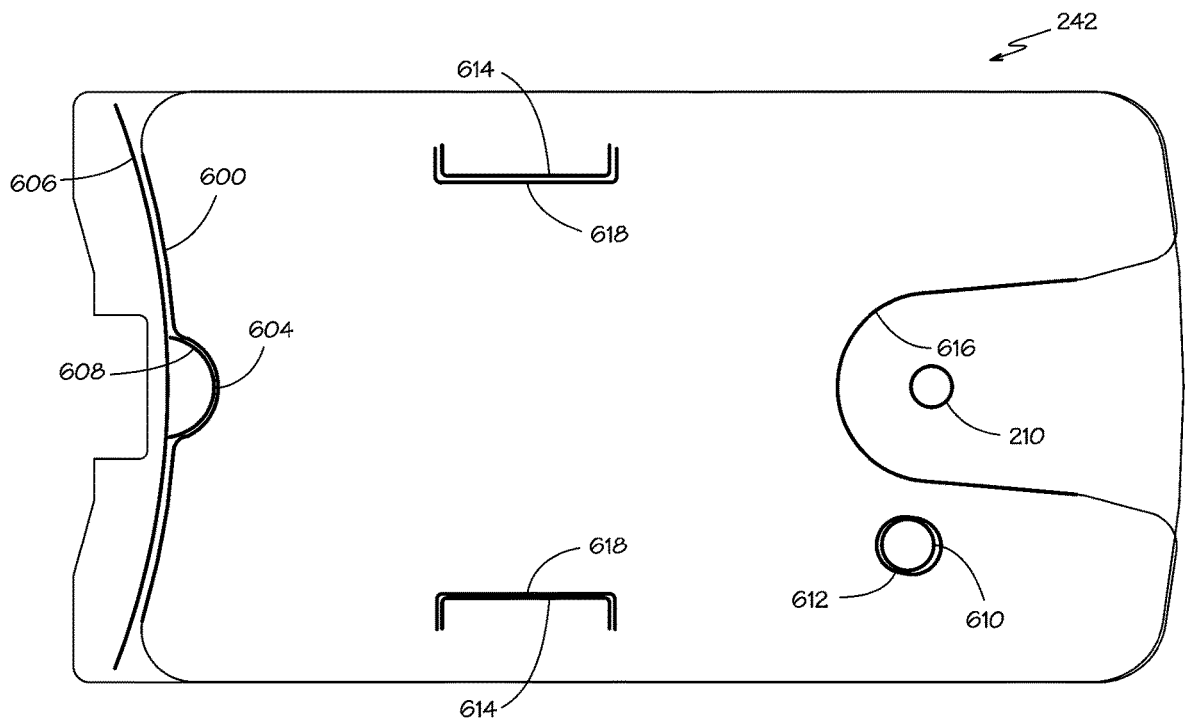

FIG. 15 shows the instrument control surface 242 when the locating pin 610 on the ISA 510 has engaged the locating slot 612 on the instrument control surface. Engaging the locating pin 610 on the ISA 510 with the locating slot 612 on the instrument control surface 242 and engaging the bullet receiving feature 604 on the instrument control surface 242 with the bullet portion 608 on the ISA 510 constrains the movement between the instrument control surface and the ISA parallel to the plane of the instrument control surface (parallel to the plane of the figure). As previously discussed, the locating pin 610 and the bullet portion 608 also provide a torque reaction feature to prevent twisting of the surgical instrument's proximal control 240 in reaction to the torques applied to the instrument by the teleoperated actuators as transmitted through the ISA 510.

While certain exemplary embodiments have been described and shown in the accompanying drawings, it is to be understood that such embodiments are merely illustrative of and not restrictive on the broad invention, and that this invention is not limited to the specific constructions and arrangements shown and described, since various other modifications may occur to those of ordinary skill in the art. The description is thus to be regarded as illustrative instead of limiting.

What is claimed is:

1. An instrument sterile adapter for coupling a surgical instrument and an instrument carriage, the instrument sterile adapter comprising:
    a control interface portion comprising:
        an adapter control surface configured to abut an instrument control surface of the surgical instrument in a mounted state of the surgical instrument to the instrument sterile adapter; and
        a carriage engaging surface opposite the adapter control surface and configured to abut a control surface of the instrument carriage in a mounted state of the instrument sterile adapter to the instrument carriage;
    one or more adapter couplers connected to the control interface portion, the one or more adapter couplers comprising:
        first adapter control features at the adapter control surface configured to engage with carriage control features of the instrument carriage in the mounted state of the instrument sterile adapter to the instrument carriage, and
        second adapter control features at the carriage engaging surface configured to engage with instrument control features of the surgical instrument in the mounted state of the surgical instrument to the instrument sterile adapter; and
    a shaft receiving slot in the control interface portion, wherein the shaft receiving slot defines a passage extending through the control interface portion from the adapter control surface to the carriage engaging surface and is configured to receive an instrument shaft of the surgical instrument in the mounted state of the surgical instrument with the instrument sterile adapter such that the instrument shaft extends through the control interface portion via the passage.

2. The instrument sterile adapter of claim 1, further comprising a transverse portion extending to the adapter control surface and coupled to the control interface portion opposite the shaft receiving slot.

3. The instrument sterile adapter of claim 2, wherein the transverse portion is configured to engage with the surgical instrument as the surgical instrument is mounted on the instrument sterile adapter to progressively guide the surgical instrument toward an installed position on the instrument sterile adapter.

4. The instrument sterile adapter of claim 3, wherein the transverse portion is configured to, in a state of engagement with the surgical instrument, constrain motion of the surgical instrument to only rotation about a first axis and translation parallel to the first axis, wherein the first axis is parallel to and offset from the instrument shaft.

5. The instrument sterile adapter of claim 4, wherein the shaft receiving slot is configured to, in a state of the transverse portion being engaged with the surgical instrument, limit rotation of the surgical instrument about the first axis.

6. The instrument sterile adapter of claim 5, wherein the transverse portion comprises:
    an engagement surface configured to initially engage with the surgical instrument as the surgical instrument is mounted to the instrument sterile adapter; and
    a guide element configured to engage with the surgical instrument subsequent to the engagement surface engaging with the surgical instrument as the surgical instrument is mounted to the instrument sterile adapter; and
    wherein the shaft receiving slot is configured to, in a state of the engagement surface of the transverse portion being engaged with the surgical instrument, limit rotation of the surgical instrument about the first axis to a first range of orientations that permit the surgical instrument to engage with the guide element.

7. The instrument sterile adapter of claim 6, wherein the guide element is configured to, in a state of engagement with the surgical instrument, further limit rotation of the surgical instrument about the first axis to a second range of orientations that is smaller than the first range.

8. The instrument sterile adapter of claim 7, further comprising:
    one or more locating features configured to engage with the surgical instrument subsequent to the guide element engaging with the surgical instrument as the surgical instrument is mounted to the instrument sterile adapter, wherein the guide element is configured to guide the surgical instrument into engagement with the locating features and the locating features are configured to further limit the rotation of the surgical instrument about the first axis to position the surgical instrument in the installed position.

9. The instrument sterile adapter of claim 7,
wherein the engagement surface of the transverse portion comprises a curved surface configured to engage with a complementary curved surface of the surgical instrument; and
wherein the guide element comprises a bullet feature protruding from the curved surface and extending parallel to the first axis.

10. The instrument sterile adapter of claim 2, wherein the transverse portion comprises a curved surface.

11. The instrument sterile adapter of claim 10, wherein the curved surface comprises a convex curved surface configured to receive a corresponding concave surface of the surgical instrument in the mounted state of the surgical instrument with the instrument sterile adapter, the convex surface being convex from a perspective at the adapter control surface.

12. The instrument sterile adapter of claim 11, further comprising a bullet portion on the convex curved surface configured to engage a bullet receiving feature in the corresponding concave curved surface as the surgical instrument is mounted to the instrument sterile adapter on the instrument control surface.

13. The instrument sterile adapter of claim 12, wherein the bullet portion comprises a tapered leading portion.

14. The instrument sterile adapter of claim 1, wherein the adapter control surface further comprises a locating pin configured to engage a locating slot in the instrument control surface as the surgical instrument is mounted to the instrument sterile adapter.

15. The instrument sterile adapter of claim 1, further comprising a locating slot in the adapter control surface configured to engage a locating pin of the instrument control surface as the surgical instrument is mounted to the instrument sterile adapter.

16. The instrument sterile adapter of claim 1, wherein the adapter control surface further comprises a plurality of landing pads configured to, in the mounted state of the surgical instrument, support the instrument control surface.

17. The instrument sterile adapter of claim 1, further comprising latch arms extending from the adapter control surface and configured to engage latch receptacles in the instrument control surface as the surgical instrument is mounted to the instrument sterile adapter.

* * * * *